(12) United States Patent
Lamb

(10) Patent No.: US 6,858,399 B2
(45) Date of Patent: *Feb. 22, 2005

(54) TEST FOR OXIDATIVE STRESS USING CELL SUSPENSIONS

(76) Inventor: Robert Lamb, 13610 Edmonthorpe Rd., Midlothian, VA (US) 23113

( * ) Notice: Subject to any disclaimer, the term of this patent is extended or adjusted under 35 U.S.C. 154(b) by 0 days.

This patent is subject to a terminal disclaimer.

(21) Appl. No.: 10/179,300

(22) Filed: Jun. 26, 2002

(65) Prior Publication Data

US 2003/0054416 A1 Mar. 20, 2003

Related U.S. Application Data

(63) Continuation-in-part of application No. 09/835,242, filed on Apr. 16, 2001, now abandoned, which is a continuation-in-part of application No. 09/160,104, filed on Sep. 25, 1998, now Pat. No. 6,218,130.
(60) Provisional application No. 60/091,082, filed on Jun. 29, 1998.

(51) Int. Cl.$^7$ .......................... G01N 33/58; G01N 33/92
(52) U.S. Cl. ............... 435/7.21; 435/2; 435/4; 435/7.25; 435/25; 435/375; 435/383; 435/384; 436/503; 436/63; 436/71; 436/901
(58) Field of Search ............................... 435/7.21, 7.25, 435/4, 25, 28, 2, 325, 375, 383, 384; 436/503, 71, 63, 901

(56) References Cited

U.S. PATENT DOCUMENTS 6,218,130 B1 * 4/2001 Lamb ........................ 435/7.21

OTHER PUBLICATIONS

Wertz et al., 1980. Inhibition of 12-O-tetradecanoylphorbol-13-acetate-accelerated phospholipid metabolism by 5,8,11,14-eicosatetraynoic acid. Cancer Res. 40: 776–781.*

Anderson et al., 1985. Role of fatty acid structure in the reversible activation of phosphatidylcholine synthesis in lymphocytes. Biochimica et Biophysica Acta 835: 360–368.*

Pacifici et al., 1994. Lipid hydroperoxide–induced peroxidation and turnover of endothelial cell phospholipids. Free Radical Biol. Med. 17: 297–309.*

Ferrali et al., 1989. Allyl alcohol–induced hemolysis and its relation to iron release and lipid peroxidation. Biochem. Pharmacol. 38: 1819–1825.*

Strunecka et al., 1988. Phospholipid biosynthesis in mature human erythrocytes. In, Gen. Physiol. Biophys. 7: 205–216. Abstract, BIOSIS No. 86000720.*

* cited by examiner

*Primary Examiner*—Christopher L. Chin
*Assistant Examiner*—James L. Grun
(74) *Attorney, Agent, or Firm*—Glenna Hendricks

(57) ABSTRACT

This invention provides a method of measuring oxidative response of cells without recourse to preparation of cell culture. The process involves:

1) preparing suspensions of cells from a living host in isotonic solutions,
2) preparing samples of test materials in isotonic solution containing tagged choline,
3) adding the cells suspension prepared in step 1 to the samples prepared in step 2,
4) incubating the product of step 3 with shaking for 2–90 minutes,
5) extracting and drying the lipid phase from the product of step 4, and
6) subjecting the product of step 5 to a scintillation counter to measure choline which has been incorporated into phosphatidylcholine (PC).

An increase in incorporation of choline into PC in the short term indicates oxidative stress or free radical induced damage. Because the method of the invention using the cell isolates does not require the expense of cell culture with concomitant expense and possibility of cell change, it is particularly useful for clinical evaluation. Furthermore, the ability to use erythrocytes for study of cellular response to oxidative stress makes it possible to test individual responses of patient using part of the blood sample drawn routinely for laboratory use.

11 Claims, No Drawings

TEST FOR OXIDATIVE STRESS USING CELL SUSPENSIONS

This application is a continuation-in-part of U.S. patent application Ser. No. 09/835,242, filed Apr. 16, 2001, now abandoned which is a continuation-in-part of U.S. patent application Ser. No. 09/160,104, filed Sep. 25, 1998, now U.S. Pat. No. 6,218,130, which takes priority from U.S. Patent Application 60/091,082 filed Jun. 29, 1998.

FIELD OF THE INVENTION

This invention provides a method for evaluation of cytotoxic effects of oxidative stress on cells while avoiding the need for growth of the cells in tissue culture. The methods of the invention make it possible to test agents such as potential drugs or other bioactive agents, such as pesticides, which may be introduced into the environment for purposes of predicting cytotoxic effects on animal populations. Using the methods of the invention, it is also possible to obtain predictive information about cellular response of the intended individual toward a given bioactive agent.

BACKGROUND OF THE INVENTION

The cells of all mammalian tissues require oxygen for respiration and oxidative metabolism. Unfortunately, the cellular reduction of oxygen results in the formation of reactive oxygen species (ROS) which are cytotoxic.

The membranes of all mammalian cells contain a phospholipid bilayer in which are imbedded various proteins that regulate drug transport, signal transduction and cellular metabolism. Phosphatidylcholine (PC) is the major membrane phospholipid. The PC contains an abundance of polyunsaturated fatty acids (PUFA) which are excellent free radical traps. Free radicals generated by cellular monooxygenases, which are imbedded in the membrane's phospholipid bilayer, produce membrane injury by interacting with the PUFA's of membrane-associated PC. The cell will die unless the free radical-induced membrane damage (alterations in PC structure) is rapidly repaired, since required cellular functions such as chemical transport, signal transduction and metabolism are disrupted. Therefore, the cell rapidly activates (by enzyme translocation) PC hydrolysis and biosynthesis to repair the injured membrane. In the healthy cell, reversible injury is repaired by rapid (5–10 minute) and significant increases (about 2–3 fold) in cellular PC biosynthesis. This process can be measured by determining the cellular incorporation of labeled choline into PC. However, free radical-induced membrane injury is only reversible as long as the rate of membrane injury is not greater than the cell's rate of membrane repair. If cells are continuously injured for extended periods, the cell's ability to make PC decreases, resulting in irreversible injury and cell death.

The "free radical" theory of cell injury has been proposed for many years to explain how cell death is produced by various conditions such as alcoholic liver disease (ALD), tissue dysfunction associated with aging, traumatic brain injury, drug-induced tissue injury, reperfusion cell damage, irradiation and exposure to UV light. Cellular levels of free radicals increase when cellular content of oxidants and antioxidants increase and decrease, respectively. The resulting injury is known as oxidative stress.

Free radicals are very reactive and can not move far from their site of formation, since they will readily interact with various cellular components such as proteins and phospholipids. The P450-dependent monooxygenases that are imbedded in the phospholipid bilayer of cellular membranes are a major source of reactive oxygen species such as superoxide anion and hydrogen peroxide that are generated during the cellular metabolism of various agents.

It is believed that the interaction of redox active ion, superoxide anion and hydrogen peroxide produce the toxic hydroxyl radical by a Haber-Weiss reaction. Cell injury occurs, in part, when the hydroxyl radical interacts with the polyunsaturated fatty acids (PUFA's) of membrane phospholipids such as PC. Free radical-induced membrane injury is repaired if PC hydrolysis and biosynthesis are rapidly increased. However, cell death occurs if PC metabolism is not increased. The above theory of cell injury as outlined in reasonable. However, determining the validity of this theory is difficult. The primary problem is that free radicals are very reactive, short-lived chemical entities. Therefore, it is difficult to measure the cellular level of free radicals and the effect of free radicals on cell functions. One way to overcome this problem is to incubate isolated hepatocellular fractions with labeled bioactive agents such as carbon tetrachloride and bromotrichloromethane (BTM) and thereafter determine the covalent binding of the trichloromethyl radical ($\cdot CCl_3$) to cellular components such as phospholipids and proteins. The trichloromethyl radical is rapidly bound covalently to the PUFA's of cellular PC. This free radical interaction can not be detected by measuring lipid peroxidation, since hydrogen abstraction has not occurred. Nevertheless, lipid peroxidation is routinely used to assess the reaction of free radicals with PUFA's, As a result, most investigators have concluded that the interaction of free radicals with cellular PC is a late, rather than early, event in the pathogenic sequence of cell death. The instant invention provides a much improved method for measuring the interaction of free radicals with cellular PC.

Previous studies have shown that oxidative stress can be induced and demonstrated in cultured cells by measurement of the incorporation of labeled choline into phosphatidylcholine. The use of cells grown in cell culture presents several problems for the investigator. First, the propagation of the cells outside of the initial, natural host results in changes in the cells. The farther in time and/or generation that the cells of the culture are from the host that supplies the cells, the more likely it is that the cells have undergone changes that alter the oxidative response. Furthermore, the culturing of some cells is often difficult, costly and time-consuming. Finally, it is quite expensive to culture cells from an individual to get a reading of how the individual host cells (as opposed to the cells generated in culture as representative of the species and cell type) will respond to a given bioactive agent.

Previous studies in tissue culture have shown that the initial response to oxidative stress is an increase in cellular phosphatidylcholine (PC) biosynthesis, which represents the cell's attempt to repair damage. In the long term, however, there is a decrease in PC biosynthesis because the cell's repair function is damaged, eventually causing cell death.

Ferrali, et al (*Biochem Pharm.*, Vol 38, No. 11, pp 1819–1825 (1989)) teaches the reporters could not demonstrate the adverse effects of allyl alcohol and acrylic acid in erythrocytes. They did manage to show deleterious effects on the cells arising from exposure to acreolein. It was suggested that the damage to the cells resulted from the effects of iron delocalization but did not provide definitive results in tests for oxidative stress from allyl alcohol. However, using the methods taught therein, those researchers were unable to show effect on erythrocytes and concluded that the enzyme required for oxidative damage from allyl alcohol was not demonstrated because the cells lacked alcohol dehydrogenase. Hence, their method did not give definitive results in tests for oxidative stress which was known to occur. This problem has been solved using the method of the invention when studying suspensions of erythrocytes.

SUMMARY OF THE INVENTION

This invention provides means of measuring oxidative response of cells without recourse to preparation of cell culture. The process consists of:

1) preparing suspensions of cells from a living host in isotonic solutions, 2) preparing samples of test materials in isotonic solution containing tagged choline, 3) adding the cell suspension prepared in step 1 to the samples prepared in step 2, 4) incubating the product of step 3 with shaking for 2–90 minutes, 5) extracting and drying the lipid phase from the product of step 4, and 6) measuring the choline which has been incorporated into PC in the product of step 5.

The method as exemplified herein for practicing step 6 involves subjecting the product of step 5 to a scintillation counter to measure choline which has been incorporated into phosphatidyl-choline (PC).

During the practice of step 5, the lipid phase may be subjected to repeated washings.

An increase in incorporation of choline into PC in the short term indicates oxidative stress or free radical-induced damage.

DETAILED DESCRIPTION OF THE INVENTION

It is the purpose of this invention to make it possible to study oxidative response on cells without resort to tissue culture. Using the processes taught herein, it is possible to obtain valuable information relating to the free radical-induced damage to the cells. It was not previously known that such testing could be done using cell suspensions.

It is particularly interesting that it is possible to use erythrocytes to measure oxidative stress arising from various toxic agents. The methods of the invention make it possible to test the effects of agents on cells of a particular patient to identify individual cellular response. The process is useful for determining the cytotoxic potential of various agents individually and in combination. Additionally, agents may be tested in combination with known toxins to determine whether they possess protective properties. When red blood cells are used, it is possible, using the process of the invention, to determine whether or not a particular agent is hemolytic.

The following PC metabolism theory of free radical-induced cell injury is proposed damage arising from exposure to alcohol. ROS ($O_2$ and $H_2O_2$) and acetaldehyde are produced by metabolism of ethanol by alcohol dehydrogenase (ADH) and cytochrome P450 2E1 (CYP 2E1). (CYP 2E1 can also metabolize other drugs such as acetaminophen.) Glutathione (GSH) is then depleted by GSH peroxidase and conjugation with acetaldehyde. Hydroxyl radicals are rapidly formed by a Haber-Weiss reaction. Thereafter, hydroxyl radicals produce cell injury by rapidly interacting with the PUFA's of membrane PC. Membrane damage is repaired if PC hydrolysis and biosynthesis are rapidly increased (reversible damage). However, cell death occurs when the rate of membrane injury exceeds the membrane's repair capacity.

Methodology

Preparation of cell suspensions: The following methods exemplify the technology (known in the literature) for isolation of cells.

Rat Hepatocytes:

Male sprague Dawley rats (Zivic-Miller) weighing 200 to 350 grams were treated with a 50 mg/kg dose of phenobarbital (ip) for 3 days prior to perfusion. During this 3 day period, the animals were also given water ad libitum containing 0.1% sodium phenobarbital. The animal was anesthetized with ether under a fume hood, then transferred to the surgical table with the abdomen exposed. The belly was shaved and cleansed with 70% ethanol and Clinidine. The abdominal skin was removed with scissors and forceps. An incision was made along the base of the abdomen and the renal artery was tied off.

After the hepatic vein was cannulated with a 16 gauge catheter, the liver was washed with a balanced salt solution containing EDTA and Tricine. The hepatic artery was cannulated with a 16 gauge catheter. After 5 minutes of reverse flow perfusion was practiced to facilitate the wash cycle. After the blood is washed from the liver, the color of the liver changes from deep red to a brownish color.

The liver was then infused with Collagenase solution (112.5 mg/300 ml of Waymouth 752/1 media) bubbled with 5% $CO_2$. After 5 minutes, reverse flow of Collagenase into the liver was accomplished, followed by reverse to normal flow after 5 minutes. Normal flow was continued until liver tissue was breaking down and ready for collection. Complete liver wash and perfusion should take about 30 minutes.

The perfused liver was collected with a strainer and transferred to an Erlenmeyer flask containing 50 ml of original Collagenase solution. The liver was minced using a gyratory water bath at 37° C. and allowed to swirl for no longer than 15 minutes. The solution was then filtered through a sterile gauze into centrifuge tubes and spun in a table top centrifuge for 5 minutes at 1000 rpm. (70×g). Aspirate media and suspended cells were placed in Waymouth 752/1 media containing 20% isodensity Percol and were then centrifuged for 4 minutes at 70×g. Cells were washed three times and resuspended in Waymouth 752/1 media. Samples of 0.5 ml were plated on 35 mm collagen-coated plastic culture dishes containing 0.75 ml of supplemented Waymouth 752/1 media.

The isolated cells were also added to test tubes containing 0.75 ml of Waymouth 752/1 media. Various agents were added and mixtures incubated at 37° C. for various periods of time as exemplified below. Incubations were terminated by the addition of 2 ml methanol. This was followed by extraction of lipids.

In an alternate method, rats were sacrificed and the liver removed by dissection. The weight of the liver was determined, and sufficient PBS was added to provide PBS equal to 4 times the liver weight. (A 10 g liver is diluted in 40 ml of PBS.) The liver was minced and homogenized. The homogenate was placed in plastic Sorval tubes, then centrifuged at 3000 rpm for 10 minutes under refrigeration (1000×g). The supernate was removed and 40 ml PBS added. This may be quickly frozen in glass test tubes in 3 ml aliquots and stored at −70° C.

Preparation of red cell fractions: Rat or human blood was placed in Sorval tubes and, centrifuged at 3000 rpm for 10 minutes under refrigeration. The supernate was removed and the pellet of RBC's resuspended in PBS at 4 times the volume of the supernate. This may be frozen in 2 ml aliquots at −70° C. (Do not freeze 3 ml aliquots as used for hepatocytes, since these will break.)

PC biosynthesis in cultured cells: Aliquots (0.01 ml) of DMSO and water or DMSO and water containing various agents were added to medium with 2-hour monolayers of cells. After the appropriate agent-incubation period, a 0.02 ml aliquot of [$^3$H]-choline (0.2 $\mu$Ci and 15 pmoles of choline]) was added to Waymouth 752/1 {1.25 ml} media. Incubations were stopped after 90 minutes by addition of 2 ml of methanol containing 1% 1N HCl. Cells were removed from the culture dishes by scraping with TEFLON™-coated spatula and placed in glass test tubes. (Lamb, et al., *Hepatology* 19: 174 (1994))

PC extraction procedure: Two ml of chloroform and 0.5 ml of water were added to each sample. Tubes were vortexed and centrifuged for 5 minutes to clear the upper and lower phases. The upper phase was aspirated and the lower phase washed by adding 2 ml of wash solution containing 50% methanol, 45% water and 5% 7.4% KCl. The samples were vortexed and centrifuged 5 minutes to clear the upper and lower phases. The upper phase was aspirated and the lower phase was washed again in 2 ml wash solution. After the phases were cleared by centrifugation, the lower phase was carefully removed, placed in a glass test tube, dried, solubilized in scintillation fluid and counted in a Beckman beta counter. Agent-induced alterations in the incorporation of labeled choline into PC was used as a measure of changes in cellular PC biosynthesis.

PC biosynthesis in isolated cells: Aliquots (0.75 ml) of Waymouth 752/1 media were placed in glass test tubes. Aliquots (0.01) of DMSO and water or DMSO and water containing various test agents were added to the tubes along with 0.02 ml [$^3$H]-choline [0.2 $\mu$Ci and 15 pmoles choline]. Incubations were started by adding 0.5 ml aliquotes of cells suspended in Waymouth 752/1 media to the test tubes and placing the tubes in a shaking water bath at 37° C. Incubations were stopped after the appropriate incubation period (2–90 minutes) by addition of 2 ml of methanol containing 1% 1N HCl. Labeled PC was extracted by methods described above for cultured cells. Agent-induced increases in the incorporation of labeled choline into PC were used to measure increases in cellular PC biosynthesis.

Waymouth 752/1 Amino Acids (without Valine) (A.A. Mix)

| Amino Acid | gm/50 liters |
| --- | --- |
| L-Aspartic Acid | 3.0 gm |
| L-Cystine | 0.75 gm |
| L-Glutamic Acid | 7.5 gm |
| Glycine | 2.5 gm |
| L-Isoleucine | 1.25 gm |
| L-Leucine | 2.5 gm |
| L-Proline | 2.5 gm |
| L-Threonine | 3.75 gm |
| L-Tyrosine | 2.0 gm |
| Cysteine | 3.05 gm |
| L-Histidine | 6.4 gm |
| L-Lysine | 12.0 gm |
| L-Tryptophan | 2.0 gm |
| L-Methionine | 2.5 gm |
| L-Phenylalanine | 2.5 gm |
| L-Ornithine | 1.0 gm |

The amino acids were mixed well with mortar and pestle. Mixture was stored at room temperature in a dark bottle.

EXAMPLE 1

Alteration in PC biosynthesis of human liver cells incubated 90 minutes with 100 mM ethanol (ETOH) or 1 mM acetaminophen ±1 mM 4-methylpyrazole was studied in accord with the methodology disclosed above. It was found that ethanol and acetaminophen significantly ($p<0.05$) increase cellular PC biosynthesis whereas 4-methylpyrazole significantly decreases the ethanol and acetaminophen-induced increases in cellular PC biosynthesis.

EXAMPLE 2

Alteration in PC biosynthesis of rat liver cells incubated 90 minutes with 100 mM ethanol or 1 mM acetaminophen ±4-methylpyrazole was studied. Ethanol and acetaminophen significantly ($p<0.05$) increased cellular PC biosynthesis whereas 4 methylpyrazole significantly reduced the ethanol-induced and acetaminophen-induced increases in cellular biosynthesis.

EXAMPLE 3

Primary cultures of adult rat hepatocytes were incubated for 72 hours with 100 mM ethanol (ETOH), 1 mM acetaminophen (APAP), or both. A significant decrease was seen in cellular PC biosynthesis potentiated by PUFA (20:4) and reduced by saturated fat (16:0), 4-methylpyrazole (4-MP), superoxide dismutase (SOD), catalase (CAT), deferoxamine (DEF) and vitamin E succinate (VES). These results suggest that ethanol and acetaminophen do not produce cell injury until they are metabolically activated by P450 monooxygenases (Note, also, inhibition of injury by 4-methylpyrazole). See Table 1.

TABLE 1

Effect of incubating (72 h) cultured hepatocytes with 100 mM ethanol (ETOH), 1 mM acetaminophen (APAP), 0.5 mM 4, methylpyrazole (4-MP), 200 units of superoxide dismutase (SOD), 800 units of catalase (CAT), 2 mM deferoxamine (DEF), 0.025 mM arachidonate (20:4) and 0.25 mM palmitate (16:0) or combinations of these agents on cellular PC biosynthesis.

| Additions | PC biosynthesis | Additions | PC biosynthesis |
| --- | --- | --- | --- |
| Control | 101 ± 6 | Control | 101 ± 6 |
| ETOH | 39 ± 2* | APAP | 42 ± 2* |
| ETOH + APAP | 15 ± 1* | | |
| ETOH + 16:0 | 95 ± 8# | APAP | 91 ± 9@ |
| ETOH + 20:4 | 18 ± 2# | APAP + 20:4 | 21 ± 2@ |
| ETOH + 4-MP | 98 ± 8# | APAP + 4-MP | 95 ± 7@ |
| ETOH + SOD | 85 ± 8# | APAP + SOD | 105 ± 10@ |
| ETOH + CAT | 78 ± 4# | APAP + CAT | 97 ± 4@ |
| ETOH + DEF | 107 ± 7# | APAP + DAF | 94 ± 6@ |
| ETOH + VES | 107 ± 10# | APAP + FES | 87 ± 11@ |

All data is expressed as a percent of control of 6–9 experimental values. All symbols indicate that values are significantly different ($p \leq 0.05$) from control (*), ETOH (#) or APAP (@) exposed cells.

All data is expressed as a percent of control of 6–9 experimental values. All symbols indicate that values are significantly different ($\leq 0.05$) from control (*), ETOH(#) or APAP (@) exposed cells.

Monooxygenases produce superoxide anion (inhibition by SOD) and hydrogen peroxide (inhibition by catalase) which interact with iron (inhibition by deferoxamine) to produce the toxic hydroxyl radical (inhibition by vitamin E succinate) by a Haber-Weiss reaction. These results suggest that the cytotoxic effects of ethanol and acetaminophen on cultured liver cells in vitro are due in part to the interaction of the toxic hydroxyl radical with the PUFA of membrane PC [potentiation by unsaturated fat (20:4) and inhibition by saturated fat (16:0)]. All of these results suggest that free radicals produce alterations in cellular PC biosynthesis. However, short-term free radical exposure produces increases in cellular PC biosynthesis whereas long-term free radical exposure (Table 1) reduces PC biosynthesis. Understanding how long-term free radical exposure disrupts membrane repair processes is fundamentally important in treating and preventing various disorders that are a result of oxidative stress such as aging, alcoholic liver disease, and drug induced tissue injury.

The use of cell suspensions for evaluation of oxidative stress has many applications. For example, in testing drugs or active agents which will be introduced into the environment, the invention can be used to determine if cells from aged or ill mammals respond differently to drug-induced oxidative stress than cells from young mammals. The methods of the invention are also useful for testing effect on cells of interactive cumulative effects of drug combinations. It is also possible, using methods of the invention, to expose freshly drawn red blood cells (RBC's) of patients who may have been exposed to undetermined drugs or toxins to other candidate active agents that might be used for treatment to determine possible effect of giving the particular candidate agents.

EXAMPLE 4

Comparison of response of cultured liver cells from older rats (20 months) with those of cultured cells from younger rats (3 months) when exposed to agents such as ethanol and acetaminophen in the manner described in Example 1 showed interesting results. Cells from young, but not from old rats, exhibit the usual ethanol- and acetaminophen-induced increase in PC biosynthesis after short-term agent exposure. However, in the cells from older rats, short-term response resembled long-term response found in cells from younger rats. Hence, it appeared the cells from the older rats progress quickly or immediately to the irreversible damage effects, essentially by-passing the reparative process indicated by increase in PC biosynthesis. (See Table 2.)

TABLE 2

Alterations in PC biosynthesis of cultured rat liver cells isolated from 3 and 20 month-old male rats incubated 24 hours with 1 mM acetaminophen (APAP) and 100 mM ethanol (ETOH).

| | Percent of control + SEM | |
|---|---|---|
| Additions | 3 Month | 20 Month |
| None | 107 ± 7 | 100 ± 3 |
| ETOH | 147 ± 13* | 59 ± 1*# |
| APAP | 137 ± 11* | 38 ± 2*# |

All data is expressed as a mean ± SEM of nine experimental values. Similar results have been obtained in cells isolated from at least three different 3 and 20 month old rats. Significance from control (*) and cells isolated from 3 month old rats (#) is $p \leq 0.05$.

The results suggest that drug-induced oxidative stress is more cytotoxic in older cells.

The data also would indicate that agents which can increase the cell's capacity to prevent the cytotoxic effects of oxidative stress may be beneficial in preventing cell dysfunction associated with aging. This conclusion was supported by the following example.

EXAMPLE 5

Alterations in PC biosynthesis were studied using cultured liver cells incubated 24 and 72 hours with and without 50 µM vitamin E phosphate (VEP). The cultured hepatocytes displayed incubation time-dependent decreases in PC biosynthesis unless vitamin E phosphate was added to the cell medium.

EXAMPLE 6

Cells were isolated from brain homogenates according to the methods described in the methodology section under "PC biosynthesis in isolated cells". Cell fractions (1,000×g) were incubated 30 minutes with 1 mM $FeSO_4$, 100 mM ethanol, 1 mM bromotrichloromethane (BTM), 1 mM Δ-9-tetrahydrocannabinol (THC) and 1 mM acetaminophen (APAP). Cells showed increase in short-term PC biosynthesis consistent with the reversible injury phase response. (See Table 3.)

TABLE 3

Agent-induced alterations in PC biosynthesis of 100 × g brain cell fractions:

| Agent | Percent control of + SEM |
|---|---|
| Control | 101 ± 4 |
| 1 mM $FeSO_4$ | 226 ± 8 |
| 100 mM ethanol | 173 ± 8 |
| 1 mM BTM | 194 ± 25 |
| 1 mM THC | 293 ± 21 |
| 1 mM APAP | 212 ± 7 |

Å values are significantly increased ($p < 0.01$) above controls.

EXAMPLE 7

The influence of agents ±4-MP on cultured astrocyte PC biosynthesis was studied. Table 4 below gives the data. The agents used were 100 mM ethanol, 1 mM 4-methylpyrazole (4-MP), 1 mM tetrahydrocannabinol (THC) and combinations of agents.

TABLE 4

| Agent | Percent control of + SEM |
|---|---|
| Control | 102 ± 8 |
| 100 mM ethanol | 199 ± 14 |
| ethanol + 4-MP | 122 ± 5 |
| 1 mM APAP | 159 ± 15 |
| APAP + 4-MP | 118 ± 5 |
| APAP + ethanol | 241 ± 23 |
| APAP + ethanol + 4-MP | 145 ± 8 |
| THC | 201 ± 11 |
| THC + 4-MP | 148 ± 9 |
| THC + ethanol | 234 ± 14 |
| THC + ethanol + 4-MP | 131 ± 5 |

Å values without 4-MP are significantly increased ($p < 0.05$) above controls. 4-MP significantly reduced ($p < 0.05$) the agent-induced increase in PC biosynthesis.

EXAMPLE 8

Rat red blood cells and human red blood cells (RBC) were tested in accord with the methods of Example 4 using various agents to evaluate short-term response to oxidative stress. Alterations in cellular function in rat RBC's after 10 minutes incubation are shown in Table 5 with results using human RBC's after 30 minutes incubation shown in Table 6. The agents used included 100 mM ethanol (ETOH), 1 mM acetaminophen (APAP), 1 mM tetrahydrocannabinol (THC) 10 mM allyl alcohol, 1 mM cocaine, and 1 mM bromotrichloromethane (BTM) all with and without 4-methylpyrazole (4-MP).

TABLE 5

Influence of agents on the rat RBC PC biosynthesis

| Agent | PC biosynthesis % of Control ± SEM |
|---|---|
| Control | 100 ± 1 |
| 100 mM ethanol | 374 ± 19 |
| 1 mM APAP | 655 ± 26 |
| 1 mM THC | 1142 ± 65 |
| 1 mM cocaine | 458 ± 7 |
| 1 mM BTM | 533 ± 29 |
| 10 mM allyl alcohol | 1315 ± 99 |
| 1 mM iron | 919 ± 73 |

Significance from control is $p < 0.05$ for all values.

TABLE 6

Drug-induced changes in PC biosynthesis of human RBC's

| Agent | PC biosynthesis percent of control ± SEM |
|---|---|
| Control | 100 ± 1 |
| 100 mM ethanol | 222 ± 9 |
| ethanol + 4-MP | 94 ± 5 |
| 1 mM APAP | 512 ± 27 |
| APAP + 4-MP | 143 ± 13 |
| 1 mM THC | 433 ± 30 |
| THC + 4-MP | 129 ± 11 |
| 10 mM allyl alcohol | 377 ± 3 |
| allyl alcohol + 4-MP | 131 ± 10 |
| 1 mM cocaine | 292 ± 10 |
| cocaine + 4-MP | 82 ± 9 |

TABLE 6-continued

Drug-induced changes in PC biosynthesis of human RBC's

| Agent | PC biosynthesis percent of control ± SEM |
|---|---|
| BTM | 728 ± 3 |
| BTM + 4-MP | 272 ± 22 |

Significance from control is p < 0.05 for all values without 4-MP. 4-MP significantly (p < 0.05) reduces all drug-induced increases in PC biosynthesis.

Significance from control is p<0.05 for all values without 4-MP. 4-MP significantly (p<0.05) reduces all drug-induced increases in PC biosynthesis.

EXAMPLE 9

Cells isolated from rat lung, spleen, kidney, brain, intestine and blood were incubated 30 minutes with 1 mM acetaminophen (APAP). It was found that 1 mM APAP significantly (p<0.05) increases PC biosynthesis in all cells. (See table 7.)

TABLE 7

Drug-induced changes in PC biosynthesis in various cells

| Tissue | PC biosynthesis percent of control ± SEM |
|---|---|
| control | 102 ± 7 |
| lung | 471 ± 38 |
| spleen | 183 ± 20 |
| kidney | 181 ± 11 |
| brain | 172 ± 14 |
| intestine | 287 ± 13 |
| erythrocytes | 236 ± 13 |

The short term (reversible injury phase) could be shown at very early stages using the fresh cell isolates. Because the method of the invention using the cell isolates does not require the expense of cell culture with concomitant possibility of cell change, it is particularly useful for clinical evaluation. Furthermore, the ability to use erythrocytes for study of cellular response to oxidative stress makes it possible to test individual responses of patient cells using part of the blood sample drawn routinely for laboratory use.

The methods of the invention are also useful for evaluation of oxidative stress-induced injury to cells from UV light, chemotherapy and irradiation. Previously, there was no technique available which could easily detect the cytotoxic effect of these stress-inducing agents and provide a means of on-going monitoring of patients' cellular response. Using methods of the invention, it is possible to test effect of cytotoxic agents and irradiation on the blood cells to determine effect of such agents on the individual's cells. As the patient's cells are exposed to these influences during therapy, it is possible to evaluate how damaging the effect of a given agent has been on normal cells.

Using the testing methods of the invention, it is possible to evaluate the individual response to environmental radiation. This is particularly valuable for persons whose work environment results in exposure to radiation. The effects of radiation on RBC's were studied using the methods of the invention. In that study, human RBC PC biosynthesis showed dose-dependent response to exposure to radiation, with about 500% increase in response at radiation dose of 10.0 rads.

It is also possible to obtain cells from individuals by biopsy or other means such as washings from the gastrointestinal and respiratory passages or from scrapings to predict cellular responses of individuals to candidate drugs or other treatment modalities.

The methods of the invention may also be used to determine whether administration of a particular drug to a patient whose history regarding pharmaceutical intervention is unknown would result in cell injury due to oxidative stress.

In addition to testing effects on mammals, the process of testing disclosed herein may also be used for testing effects of agents on birds, fish and mammal. Such testing is particularly valuable in study of agents that will be introduced into the animal's environment.

What I claim is:

1. A method of evaluating potential oxidative stress and/or cytotoxic response changes on cells from a particular individual to at least one agent of interest comprising the steps of:

1) obtaining a sample containing cells from said individual and, without intervening tissue culture, preparing at least two suspensions of said cells from said sample in isotonic solutions;

2) preparing a control solution containing detectably labelled choline, and adding one of said at least two non-cultured suspensions thereto to form a control suspension;

3) preparing at least one test solution each containing detectably labelled choline and said at least one agent of interest, then adding a different one of said at least two non-cultured suspensions to each of said at least one test solution to form at least one test suspension;

4) incubating said control and at least one test suspensions for 2–90 minutes under conditions suitable for incorporation of said detectably labelled choline into phosphatidylcholine in a lipid phase of the said individual's cells therein;

5) stopping said incubating by adding an organic solvent to each of the control and test suspensions;

6) extracting and drying the lipid phase of the cells in each of said stopped control and test suspensions; and 7) detecting and measuring labelled choline incorporated into each lipid phase, and comparing a level of choline incorporation into phosphatidylcholine measured in the lipid phase of cells in said at least one test suspension to a level of incorporation measured in said control suspension, to identify differences in the levels of labelled choline incorporation in order to evaluate oxidative stress and/or cytotoxic response effects induced by said at least one agent of interest on the cells of said individual.

2. The method of claim 1 wherein the individual is a patient.

3. The method of claim 1 wherein the sample is blood.

4. The method of claim 3 wherein the cells are erythrocytes.

5. The method of claim 1 wherein the sample containing cells is a washing from gastrointestinal or respiratory passages.

6. The method of claim 1 wherein the sample containing cells is obtained by scraping.

7. The method of claim 1 wherein, in step 6, the lipid phase, after extraction, is washed before drying.

8. The method of claim 7 wherein the lipid phase is washed at least 3 times before drying.

9. The method of claim 1 wherein at least one agent of interest in step 3 is an agent suspected of producing red blood cell lysis in patients with glucose-6-phosphate dehydrogenase deficiency.

10. The method of claim 2 wherein the patient has received chemotherapy.

11. The method of claim 2 wherein the patient has been exposed to radiation.

* * * * *